United States Patent [19]

Bornat

[11] 4,323,525
[45] Apr. 6, 1982

[54] ELECTROSTATIC SPINNING OF TUBULAR PRODUCTS

[75] Inventor: Alan Bornat, Liverpool, England

[73] Assignees: Imperial Chemical Industries Limited, London; University of Liverpool, Liverpool, both of England

[21] Appl. No.: 31,606

[22] Filed: Apr. 19, 1979

[30] Foreign Application Priority Data

Apr. 19, 1978 [GB] United Kingdom ............... 15419/78

[51] Int. Cl.³ ..................... B29D 23/00; A61F 1/00; A61B 17/00; B29C 13/00
[52] U.S. Cl. ........................................ 264/24; 3/1.4; 128/334 R; 264/22; 425/174.8 E
[58] Field of Search ................. 264/26, 159, 313, 234, 264/24, 22; 249/183; 128/334 R; 427/185; 425/174.8 E; 3/1.4

[56] References Cited

U.S. PATENT DOCUMENTS

| | | | |
|---|---|---|---|
| 2,241,125 | 5/1941 | Girard | 249/183 |
| 3,851,838 | 12/1974 | Biggs et al. | 242/118.32 |
| 3,910,513 | 10/1975 | Gelin et al. | 242/118.32 |
| 4,044,404 | 8/1977 | Martin et al. | 3/1.4 X |

FOREIGN PATENT DOCUMENTS

2444715 4/1975 Fed. Rep. of Germany ...... 249/183

*Primary Examiner*—F. Edmundson
*Attorney, Agent, or Firm*—Cushman, Darby & Cushman

[57] ABSTRACT

A process for electrostatically spinning fiber forming material. The spun fiber is collected on a removable sheath on a rotating mandrel. The sheath is electroconductive. The tubular spun fiber product is separated from the sheath.

13 Claims, 1 Drawing Figure

ELECTROSTATIC SPINNING OF TUBULAR PRODUCTS

This invention relates to tubular products and to processes for the production thereof.

British Patent Application No 4407/76 and German OLS DT 2704771 A1 describes the preparation of tubular products, for example, vascular prostheses, by a process involving the electrostatic spinning of liquids, e.g. solutions of fibre-forming materials, to give fibres which are then collected upon a shaped former, which may be a rod or tube of configuration corresponding to that which it is desired to impart to the internal surface of the product. The fibres obtained by this process are thin, usually of the order of 0.1 to 25 $\mu$m, preferably 0.5 to 10 $\mu$m and more preferably 1.0 to 5 $\mu$m and particularly preferably 1 $\mu$m±20%.

The process of electrostatic spinning involves the introduction of a liquid into an electric field whereby the liquid is caused to produce fibres. After being drawn from the liquid the fibres harden, which may involve mere cooling (where the liquid or a component thereof is normally solid at room temperature, for example), chemical hardening or evaporation of solvent, and the hardening or hardened fibres may be collected upon a suitably charged surface.

The above mentioned patent application describes inter alia the production of tubular fibrous products using the technique of electrostatic spinning, and particularly electrostatic spinning of fibre-forming polymer containing liquid compositions comprising a polyurethane, so that tubular products comprising polyurethane fibres are obtained. One example of such tubular product is a vascular prosthesis, particularly a synthetic blood vessel. Other applications for such tubular products include use as ducts of a variety of kinds, e.g. urinary, air or bile as well as 'conduit' through which for example a wire or other device or structure may pass or lie.

Occasionally difficulty has been experienced in removing the spun tubular product from the former. This is particularly the case where the lumen of the tube is small (particularly less than, e.g. 1 cm, and especially less than 5 mm I.D.), or where the tube is long, or thin-walled or fragile, and we have therefore found it advantageous to spin the tube onto a former consisting of a core and a sheath of suitable material and configuration.

Accordingly the present invention provides a method of preparing a tubular product by electrostatically spinning a fibre forming material and collecting the resulting spum fibres on a former, the former comprising a core and a sheath therefor.

By 'former' we mean a structure upon which the electrostatically spun fibres are collected and which imparts to the resulting product, comprising the mass of collected fibres, a desired configuration. The core which serves to maintain the desired configuration of the sheath and if necessary to impart motion to it is conveniently a mandrel of substantially cylindrical configuration and of diameter approximately to the desired internal diameter of the spun tubular product. The core preferably is electrically conducting and more preferably is a metal, although electrical conduction may not be essential if the sheath is appropriately conducting in which case the core may be of any suitable material including plastics material. The core, which may be hollow or solid, preferably has a smooth surface to facilitate sliding of the sheath upon the core when it is to be removed therefrom, although to prevent undesirable slip between the core and sheath, when, for example, the sheath is to be rotated during collection of the fibres, it may be desirable to encourage a degree of friction between the core and the sheath, for example by roughening the surface of the core, particularly so as to reduce slip in a rotational direction around the long axis of the core, not in a longitudinal direction. This may be accomplished for example, by lightly grooving the surface of the core in a direction parallel to its long axis. The core will conveniently be mounted so that it may be rotated around its long axis and provided with electrical contacts so that its electrical charge (which may be at earth potential) may be adjusted as required.

The sheath preferably comprises a suitably non-electrically conducting material, most conveniently a metal so that when the former (core, sheath or both as appropriate) is charged in relation to the fibres, the fibres of the electrostatically spun material will be attracted to it and collect upon its surface. Preferably the sheath will be made of sheet metal, or metal foil, although the use of a sheath made of fibrous material, e.g. polymer, some or all of the fibres preferably being electrically conducting, or polymeric or other sheet or tube material is not excluded. Most preferably the sheath will be made of metal foil of such a thickness that it can easily be deformed, and preferably collapsed so that it is capable of being withdrawn conveniently from the lumen of a tube spun upon it. We do not exclude the possibility that the sheath comprises localised thickening or contouring as may be required for example to impart a desired contour or a particular configuration to the product of the process. For example it may be desirable for the sheath to have one or more rigid extremities which may facilitate its handling and which can be detached, e.g. by cutting, removing the sheath from the tubular product. It is sometimes advantageous to coat at least part of one or both surfaces of the sheath with a suitable slip enhancing material e.g. fluorinated hydrocarbon to facilitate its removal from the core and/or tubular product, although this coating must not be such that the efficiency of the process of the invention is not unduly impaired for example by an insulating effect.

The major part of the sheath, then, should preferably be deformable and more preferably collapsible. Conveniently it will comprise a metal foil, conveniently of thickness between 0.005 mm and 1 mm, preferably between 0.01 mm and 0.5 mm and more preferably between 0.01 mm and 0.025 mm. Most metals are suitable provided of course, that they do not react undesirably with any material with which they contact in the course of the process of the invention, thay they are appropriately stable under the conditions of the process, and that they do not tend easily to contaminate the product undesirably, e.g. with toxic metal residues. Aluminum foil and tin foil are preferred metals.

Removal of the sheath from within the tubular product is preferably preceded by collapse of the sheath, for example by crushing it gently although it may be removed by dissolution in a suitable solvent for the sheath (which solvent must obviously not undesirably affect the product).

Most conveniently the sheath will be wrapped around the core so that after removal of the sheath and tubular product from the core an edge of the sheath may be gripped and the sheath wound to release it from the product.

Materials suitable for the preparation of tubular products according to the invention include polymeric substances and in particular biologically acceptable polymeric substances. By biologically acceptable we mean substances that do not decompose or otherwise react undesirably when in contact with biological tissue with which they are likely to come into contact in use, for at least a useful period of time. As preferred substances we would mention fluorinated hydrocarbons, e.g. PTFE which conveniently may be spun from a dispersion of the material in a suitable dispersing agent, and polyurethanes which may be spun from solution, although other biologically acceptable polymers which can be electrostatically spun to give fibres are not excluded.

The tubular products prepared according to the present invention may be spun from a solution of or a dispersion of a polymer or precursors thereof when these can later be converted into the polymer. Polymers which may be conveniently spun from solution include high molecular weight fibre forming thermoplastics; in particular we would mention polyurethanes, polyamides and polyacrylonitrile. Polymers which may conveniently be spun from dispersion include polytetrafluoroethylene and polyesters as well as those listed above. As an example of a polymer precursor which may be spun from solution we mention urea formaldehyde which may be cross-linked subsequent to spinning by treatment with acid vapour.

Water soluble polymers, e.g. polyvinyl alcohol, polyvinyl pyrrolidone, and polyethylene oxide, may be spun from aqueous solution. While we do not exclude the possibility that tubes prepared from such materials may be used as prepared, preferably such tubes are given at least a degree of insolubility in aqueous medium e.g. by cross-linking the polymer with a suitable reagent after spinning.

Where the products of the invention are spun from a dispersion the spinning material comprises preferably also a solution of an additional component which acts to enhance the viscosity of the suspension and to improve its fibre forming properties. Most convenient for this purpose, we have found, is an additional organic polymer material.

The preferred spinning material, then, is a solution or suspension which preferably comprises an organic polymer in an amount such that it is capable of forming a fibre and has cohesion properties such that the fibre form is retained during any post fibreization hardening until the fibre has hardened sufficiently not to lose its fibrous shape on detachment from a support where this is appropriate.

Where tubes are spun from solution they comprise point bonded fibres and are often strong enough for use without any further treatment.

Where the tubes are spun from dispersion they often have a tendency to be friable, being mere agglomerations of discrete particles held together in the form of fibres by the additional organic polymeric component present. Preferably such tubes are sintered so that the particles soften and flow into each other and the fibres may become point bonded. In the case of PTFE sintering may conveniently be carried out between 330° C. and 450° C. preferably between 370° C. and 390° C. Sterilisation may proceed concurrently during the sintering process. The sintering temperature in the case of PTFE is usually sufficiently high to destroy completely any undesirable organic component in the final product, e.g. material added solely to enhance viscosity or emulsifying agent.

The additional organic component need be employed only in a relatively small proportion (usually within the range 0.001 to 12% and preferably 0.01 to 3%) by weight of the suspension, although the precise concentration for any particular application can easily be determined by trial.

The degree of polymerisation of the additional organic component where it is employed is preferably greater than about 2000 units linearly; a wide range of such polymers is available. An important requirement is solubility of the polymer in the selected solvent or suspending medium which is preferably water. As examples of water-soluble polymeric compounds we may mention polyethylene oxide, polyacrylamide, polyvinyl pyrrolidone and polyvinyl alcohol; where an organic medium is employed to prepare the spinning material, either as the sole liquid solvent or as a component thereof, a further wide range of organic polymeric compounds is available, for example, polystyrene and polymethylmethacrylate.

The degree of polymerisation of the polymer will be selected in the light of required solubility and the ability of the polymer to impart the desired properties of cohesion and viscosity to the fibreizable liquid.

We have found that generally the viscosity of the fibreizable liquid whether due solely to the presence of the fibreizable polymer or partly contributed to by the additional organic polymer should be greater than 0.1 but not greater than 150 poise. Preferably it is between 0.5 to 50 poise and more preferably between 1 and 10 poise, (viscosities being measured at low shear rates and at the spinning temperature). The viscosity required using a given additional organic polymer will vary with the molecular weight of the polymer, i.e. the lower the molecular weight the higher the final viscosity needed. Again, as the molecular weight of the polymer is increased a lower concentration of it is required to give good fibreization. Thus, as examples we would mention that in the preparation of polytetrafluoroethylene tubes we have found that using a polyethylene oxide of MW 100,000 as the additional organic polymer a concentration of about 12% by weight relative to the PTFE content is needed to give satisfactory fibreization whereas with a MW of 300,000 a concentration of 1 to 6% may be adequate. Again, at a MW of 600,000 a concentration of 1 to 4% is satisfactory, while at a MW of $4 \times 10^6$ a concentration as low as 0.2% may give good fibreization.

The concentration of the fibreizable polymer will depend upon the amount required to provide adequate fibre properties, and will be influenced also by the need to produce a liquid of appropriate viscosity and speed of fibre hardening. Thus in the case of a dispersion we may use a concentration within the range 25% w/w to saturation (in the case of dispersion, 'saturation' means the maximum concentration which may be included without destroying the useful spinnability of the liquid) preferably 40 to 70% and more preferably 50 to 60%, and in the case of a solution we may use a concentration within the range 8 to 60% w/w, preferably 10 to 20% w/w.

It will be appreciated that the concentration of the components must each be adjusted to take account of the presence and concentration of any other and their relative effects upon viscosity, etc.

The spinning material should have some electrical conductivity, although this may vary between quite wide limits; for example we prefer to employ solutions having conductivity within the range $1 \times 10^{-8}$ to $5 \times 10^{-2}$ mhos cm$^{-1}$.

Any convenient method may be employed to bring the spinning material into the electrostatic field, for example we have supplied the spinning liquid to an appropriate position in the electrostatic field by feeding it to a nozzle from which it is drawn by the field, whereupon fibreization occurs. Any suitable apparatus can be employed for this purpose, thus we have fed the spinning material from a syringe reservoir to the tip of an earthed syringe needle, the tip being located at an appropriate distance from the electrostatically charged surface of a former. Upon leaving the needle tip the material forms fibre between the needle tip and the former.

Droplets of the spinning liquid may be introduced into the field in other ways, which will be apparent to the skilled man, the only requirement being that they can be held within the field at a distance from the electrostatically charged surface such that fibreization occurs. For example they could be carried into the field on say, a continuous carrier, e.g. a metal wire.

It will be appreciated that where the liquid is fed into the field through a nozzle, several nozzles may be used to increase the rate of fibre production. Alternative means of bringing the fibreizable liquid into the charge field may be employed, for example a slot or a perforated plate (the perforations being fed with fibreizable liquid from a manifold) may be employed.

The electrostatic potential employed will usually be within the range 5 Kv to 1000 Kv, conveniently 10–100 Kv and preferably 10–50 Kv over a distance of 7–15 cm. Any appropriate method of producing the desired potential may be employed.

To allow high production rates, hardening of the fibres should occur rapidly and this is facilitated by the use of concentrated fibreizing liquids (so that the minimum liquid has to be removed), easily volatile solvents (for example the liquid may be wholly or partly of low boiling organic liquid) and relatively high temperatures in the vicinity of the fibre formation. The use of a gaseous, usually air, blast, particularly if the gas is warm, will often accelerate hardening of the fibre; conveniently such a blast is counter-current. Careful direction of the air blast may also be used to cause the fibres, after detachment, to lay in a desired position or direction. However, using conditions as described in the Example no particular precautions were needed to ensure rapid hardening of PTFE fibres. We found that during its formation and travel from the nozzle to the belt sufficient hardening (dehydration in the case described) occurred at ambient temperature without the need for auxiliary hardening treatment, but in the production of other fibres e.g. polyurethanes, elevated temperature and counter-current air flow may be advantageous.

Tubes prepared according to the present invention may have walls between a few microns and a few centrmeters thick, the choice of thickness will depend on the particular application and will be selected in the light of experience of the strength of the product after spinning and the conditions to which it will be exposed. However, we have found that when using polyurethane as the fibres the thickness of wall for use as a vascular graft will usually be within the range 5–25% preferably 9–18% and more preferably 10–12% of the internal diameter of the lumen. Spinning will usually, therefore be continued until a wall of desired thickness has been deposited, taking into consideration any dimensional charges which may result from shrinkage e.g. on drying or cross-linking, or from elastic contraction of the fibres.

The pore size of the tubes prepared according to the invention will usually be between $0.001\mu$ and $500\mu$. For the tube to be sufficiently porous to allow penetration of cells into the surface layers, preferably the average surface pore dimension should be of the order of 5 to $25\mu$ particularly preferably between 7 and $15\mu$, although pore size in the bulk of the material may average about 1 $\mu$m.

The invention is particularly useful in providing novel synthetic blood vessels or components thereof. Conveniently such synthetic vessels consist of tubes, preferably of circular cross-section, which may be of the constant diameter along their length or may be of varying diameter or configuration, for example they may taper or they may include constrictions or grooves to facilitate their location. Such tubes may be of dimensions and configuration appropriate to the intended function and location in which they are to be employed, for example as a replacement for a diseased blood vessel, and they may, of course, be prepared upon a mandrel of corresponding dimensions and configurations.

Such synthetic vessels may be of the order of 0.1 to 3 cm, preferably 0.2 to 2 cm, and more preferably 0.3 to 0.8 cm in internal diameter. The thickness of the wall of the vessel may vary between wide limits, and will depend inter alia upon the strength and elasticity required in the tube as well as the need for it to be convenient to locate and affix. Usually the thickness of the vessel wall will be within the range 0.1 to 2 mm, preferably between 0.1 to 1 mm.

The synthetic vessel of the invention may be of any of a variety of configurations, for example it may be a straight or bent tube, a loop, an enastomosis or it may be bifurcate. Such forms may be obtained by spinning upon a former of suitable shape.

The preferred vessels comprise fibres of an appropriate polyurethane selected from the wide range of materials available on the basis of ease of fabrication, lack of toxicity, solubility, mechanical properties, degree of biodegradability, etc. While it is preferred that a completely polymerised polyurethane dissolved in a suitable solvent (together with other additives as required) is used as the spinning solution we do not exclude the possibility of spinning incompletely polymerised polyurethane, completion of polymerisation being effected during or after spinning.

Particular uses of synthetic blood vessels obtained by the process of the invention in animals including man include:

(a) arterio-venous shunts for use in renal dialysis
(b) thin-walled prostheses for replacement of veins e.g. portal vein
(c) construction of pulmonary vessels in congenital heart malformation
(d) replacement of small bore arteries (less than 8 mm I.D.)

The invention is further illustrated in the attached drawings, in which.

EXAMPLE 1

Figure 1:
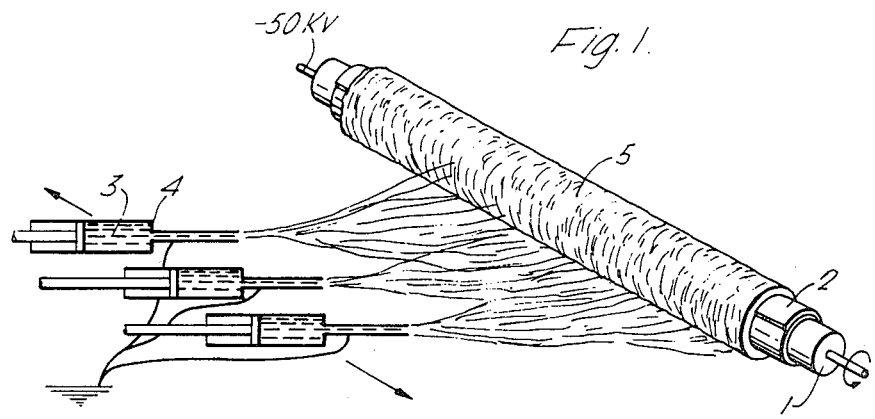
FIG. 1 represents diagrammatically the electrostatic spinning of a liquid onto a former.
Figure 2:
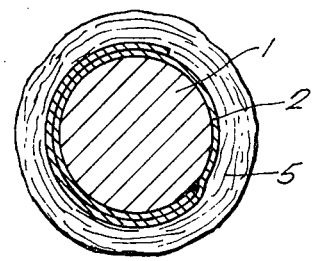
FIG. 2 is a cross-section of the mandrel/sheath/prosthesis.

The apparatus was as shown diagrammatically in FIG. 1. The former onto which the fibres were collected consisted of a metal mandrel or core (1) 20 mm in diameter and 25 cm long having a sheath of aluminium foil (2) 0.02 mm and 20 cm long wrapped around it. The former, which was charged to 50 Kv, was rotated about its long axis at about 300 rpm.

The fibre forming material (3) was fed into the electric field surrounding the former from a bank of 3 syringes (4), the needles of which were 3 cm long and 0.05 cm I.D. at the rate of 1 gm/hr/needle. The fibre forming material was a 15% solution polyether urethane block copolymer in DMF/Butanone (3:2 w/w) solution. The dried solid polymer had a hardness within the range 30°–40° shore D.

Upon introduction of the polymer into the electric field the droplet instantly disintegrated into fibres which were drawn to the mandrel, (over a distance of 10 cm against a counter current of air at 40° C. moving at about 50 ft/min) and deposited upon it in a tubular layer (5).

Figure 3:
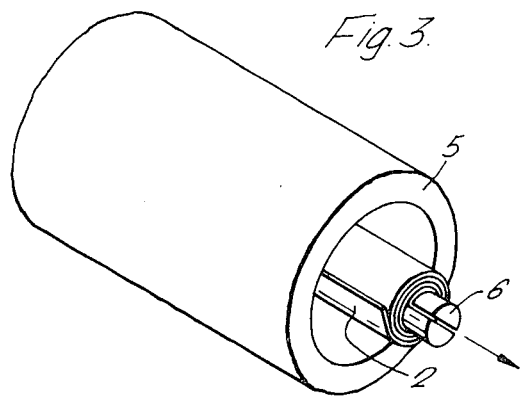
FIG. 3 shows diagrammatically the removal of the rolled sheath from the lumen of the prosthesis.

After allowing the layer to attain a thickness of about 2 mm the process was stopped, the former was removed from the apparatus, the aluminium sheath and product slid off the mandrel and the long edge of the sheath gripped between rods (6) inserted into the lumen of the tube and the sheath rolled more tightly upon the rods and removed from the lumen of the fibrous tube (see FIG. 3).

EXAMPLE 2

The process of Example 1 was repeated, except that the outside of the aluminium foil sheath was coated with PTFE spray-on release agent which facilitated release of the fibrous tube, the I.D. of the product obtained was 4 mm the wall thickness was 0.5 mm, spinning being effected through a bank of 3 needles, each delivering 1 gm of solution/hour.

I claim:

1. A method of preparing a tubular product by electrostatically spinning a fibre-forming material and collecting the resulting spun fibres upon a former, the former comprising a core and a removable sheath thereon.

2. A method according to claim 1 in which the core is a substantially cylindrical mandrel.

3. A method according to claim 1 in which the sheath comprises an electrically conducting material.

4. A method according to claim 3 in which the sheath is metallic.

5. A method according to claim 4 in which the sheath is a deformable metal sheet or foil.

6. A method according to claim 5 in which the sheath comprises aluminium or tin.

7. A method according to claim 1 in which at least part of one or both surfaces of the sheath are coated with a non-insulating film of a slip-enhancing material.

8. A method according to claim 7 in which the coating comprises a fluorinated hydrocarbon.

9. A method according to claim 1 further comprising using a sheath material having a thickness between 0.005 and 1 mm.

10. A method of preparing a tubular product which comprises the steps of applying a non-insulating sheath to a substantially cylindrical core to form the former, electrically charging the former, electrostatically spinning a fibre-forming material and collecting the fibres upon the sheath, removing the sheath and product from the core, and removing the sheath from within the lumen of the tubular product.

11. A method according to claim 10 in which the sheath is removed from the lumen of the product by compressing or by rolling the material of the sheath to reduce its diameter relative to the lumen, followed by withdrawal from the lumen.

12. A method according to claim 11 in which rolling of the material of the sheath is effected by inserting into the lumen of the product held upon the sheath rods capable of being brought together to grip the free long edge of the sheath, gripping the edge with the rods and rolling the sheath tightly upon them.

13. A method according to claim 11 or claim 12 which comprises using a lumen of the fibrous tube of less than 1 cm in diameter.

* * * * *